United States Patent [19]

Williams

[11] Patent Number: 4,917,601
[45] Date of Patent: Apr. 17, 1990

[54] ORTHODONTIC EXPANSION SCREW APPLIANCE

[75] Inventor: Jeff I. Williams, Memphis, Tenn.

[73] Assignee: Professional Learning Programs, Inc., Memphis, Tenn.

[21] Appl. No.: 305,284

[22] Filed: Feb. 2, 1989

[51] Int. Cl.$^4$ ............................................. A61C 3/00
[52] U.S. Cl. .......................................................... 433/7
[58] Field of Search .............................................. 433/7

[56] References Cited

U.S. PATENT DOCUMENTS

| 3,022,197 | 2/1962 | Jedlicka | 411/258 |
| 3,061,455 | 10/1962 | Anthony | 411/258 |
| 3,069,387 | 12/1962 | Allen et al. | 252/49.7 |
| 4,054,996 | 10/1977 | Wallshein | 433/7 |
| 4,347,054 | 8/1982 | Kraus et al. | 433/7 |
| 4,354,832 | 10/1982 | Wallshein | 433/7 |
| 4,482,318 | 11/1984 | Forster | 433/7 |
| 4,576,847 | 3/1986 | Tajima | 428/67 |

FOREIGN PATENT DOCUMENTS 1250054 9/1967 Fed. Rep. of Germany .......... 433/7

Primary Examiner—John J. Wilson
Assistant Examiner—Adriene J. Lepiane
Attorney, Agent, or Firm—Walker & McKenzie

[57] ABSTRACT

An orthodontic expansion screw appliance for being secured to first and second areas of a patient's teeth. The appliance includes a first screw body attached relative to the first area of the patient's teeth; a second screw body attached relative to the second area of the patient's teeth; a screw spindle having a threaded first end for being screwed to the first screw body and having a threaded second end for being screwed to the second screw body; rotation of the screw spindle causing the first and second screw bodies to move relative to one another; and fill structure coating the threaded first and second ends of the screw splindle for preventing the externally threaded first and second ends of the screw spindle from inadvertently rotating relative to the screw bodies.

6 Claims, 1 Drawing Sheet

ORTHODONTIC EXPANSION SCREW APPLIANCE

BACKGROUND OF THE INVENTION

1. Field of the Invention

The present invention relates, in general, to orthodontic expansion appliances and more specifically to a non-slip orthodontic expansion screw.

2. Information Disclosure Statement

A preliminary patentability search in class 433, subclass 7 and class 411, subclass 914 disclosed the following patents which may be relevant to the present invention: Jedlicka, U.S. Pat. No. 3,022,197, which discloses spreading a siloxane elastomer between the threads of screws, bolts or the like and corresponding threaded receptacles to adhesively bond the parts together so that shocks, vibrations, etc., will not cause loosening of such connections; Anthony, U.S. Pat. No. 3,061,455, which discloses applying a first chemical compound on the threads of a bolt or the like and applying a second chemical compound on the threads of a coacting nut or the like so that when the two parts are screwed together the two compounds will unit by chemical action to oppose the separation of the two parts; Allen et al, U.S. Pat. No. 3,069,387, which discloses a thixotropic thread lubricant for reducing the galling between threaded members of stainless steel, aluminum and the like and employs a relatively high concentration of Teflon; and Tajima, U.S. Pat. No., 4,576,847, which discloses a threaded member made of fiber-reinforced plastic having at least the threaded portions coated with a crosslinked nylon resin to enable the smooth meshing of a nut or the like with a bolt or the like with a coacting threaded member without jolting. Further, the present inventor is aware of Kraus et al, U.S. Pat. No. 4,347,054, which discloses an orthodontic expansion screw. None of the above patents disclose or suggest an orthodontic expansion screw appliance including a first screw body having an internally threaded bore; first retention means attached to the first screw body for attaching the first screw body relative to a first area of the patient's teeth; a second screw body having an internally threaded bore; second retention means attached to the second body for securing the second screw body relative to a second area of the patient's teeth; a screw spindle having an externally threaded first end for being screwed into the internally threaded bore of the first screw body and having an externally threaded second end for being screwed into the internally threaded bore of the second screw body; rotation of the screw spindle causing the first and second screw bodies to move relative to one another; and fill means positioned between the internally threaded bores of the first and second screw bodies and the externally threaded first and second ends of the screw spindle for preventing the externally threaded first and second ends of the screw spindle from inadvertently rotating within the internally threaded bores of the screw bodies.

Additionally, the inventor is aware of a "Scheu" expansion screw in which a threaded plastic sleeve is screwed onto the screw spindle in an attempt to reduce slippage; the "Scheu" expansion screw is used in a removal-type appliance in which the screw is embedded into acrylic for retention to the teeth.

None of the known prior orthodontic expansion appliances, such as the one disclosed by Kraus et al, addresses the problem of slip-back, nor have Teflon threads been used on any type of orthodontic screw appliance in the prior art.

The Jedlicka, Anthony and Tajima patents address the problem of thread slippage primarily by locking the screw threads in fixed positions by use of adhesive-type compounds.

The Allen patent which uses Teflon coatings on screw threads has as its object to lubricate particularly tight fittings in an effort to prevent galling of the threaded parts.

SUMMARY OF THE INVENTION

The present invention is directed toward providing an improved orthodontic expansion screw appliance.

Few orthodontic appliance problems are as exasperating as an expansion appliance that slips back during treatment, necessitating appliance removal and reworking. The cost to the practitioner in lost chair time and laboratory time are only part of the problem—the patient loses time and confidence as well.

Even the most expensive expansion screw appliances have inconsistencies in the tolerance between the machined parts. Coupled with the intra-oral flexing the appliance receives, the result is a loosened screw spindle that slips back during treatment, halting treatment progress.

The preferred embodiment of the present invention solves this problem with a unique combination that utilizes a high-quality screw body and specially coated screw threads which eliminate the tolerance gap and cushion the intra-oral flexing effect. The result is an expansion appliance that operates with consistently firm resistance to turning, yet exceedingly smooth, non-binding action.

One object of the present invention is to use the unexpected property of a fluorocarbon resin coating (e.g., Teflon, Teflon S, Supra Silverstone, TFE, FEP, PFA, etc.) to tighten an otherwise unacceptably loose threaded orthodontic fitting, the opposite of what the prior art teaches.

Another object of the present invention is to address the use of threaded parts that are continually and gradually in motion during use, as opposed to the previously described situations where threaded parts are to be screwed together initially and left in the fixed position indefinitely.

Another object of the present invention is to use a material that is inert and safe to be used in the human mouth.

The concept of the present invention is to coat the screw threads of the screw spindle of an orthodontic expansion screw appliance with fill means to provide a tighter fit which will not slip during several months in a patient's mouth. The screw spindle is turned one-fourth of a turn at a time in the patient's mouth. After several months the screw spindle of prior appliances often becomes so loose it slips backwards and prevents treatment progress. The fluorocarbon resin coating on the screw threads of the preferred embodiment of the present invention will fill in the tolerance gap between the screw and its threaded housing, making it tighter and less likely to slip but still allowing smooth turning of the screw. In addition, the fluorocarbon resin coating on the screw threads will absorb some of the flexing that the appliance receives in the mouth and will therefore resist the effect of a widening gap between the coacting threads of the screw spindle and the screw bodies as the months go by.

The orthodontic expansion screw appliance of the present invention includes a first screw body having an internally threaded bore; first retentio means attached to the first screw body for securing the first screw body relative to a first area of the patient's teeth; a second screw body having an internally threaded bore; second retention means attached to the second screw body for securing the second screw body relative to a second area of the patient's teeth a screw spindle having an externally threaded first end for being screwed into the internally threaded bore fo the first screw body and having an externally threaded second end for being screwed into the internally threaded bore of the second screw body; rotation of the screw spindle causing the first and second screw bodies to move relative to one another; and fill means coating the externally threaded first and second ends of the screw spindle for preventing the externally threaded first and second ends of the screw spindle from inadvertently rotating within the internally threaded bores of the screw bodies.

DESCRIPTION OF THE PREFERRED EMBODIMENT

Figure 1:
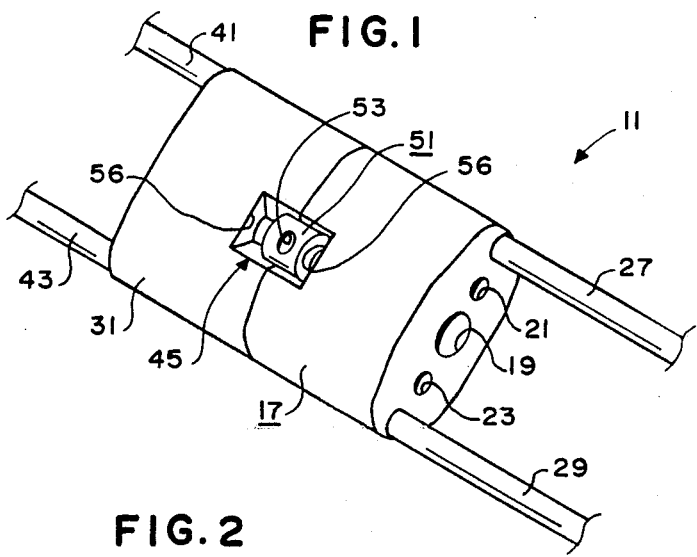
FIG. 1 is a perspective view of the orthodontic expansion screw appliance of the present invention.

The preferred embodiment of the orthodontic expansion screw appliance 11 of the present invention is used to correct dental misplacement by being secured to a first area 13 and a second area 15 of a patient's teeth to normally expand or stretch the distance between the first and second areas 13, 15.

The appliance 11 includes a first screw body 17 having an internally threaded bore 19. The first screw body 17 may consist of a rigid metal body having a smooth surface and rounded corners, etc., as will now be apparent to those skilled in the art. The threaded bore 19 is preferably located through the longitudinal center of the screw body 17. The screw body 17 preferably has a first unthreaded bore 21 extending therethrough parallel to and on one side of the threaded bore 19 and a second unthreaded bore 23 extending therethrough parallel to and on the other side of the threaded bore 19 as clearly shown in FIG. 3.

The appliance 11 includes a first retention means 25 attached to the first screw body 17 for securing or attaching the first screw body 17 relative to the first area 13 of the patient's teeth. The first retention means 25 may consist of a first arm member 27 and a second arm member r29 attached at one end to the first screw body 17 and attachable at the other end to the first area 13 of the patient's teeth. More specifically, each arm member 27, 29 may consist of a substantially rigid but bendable metal rod or the like with one end thereof soldered or otherwise fixedly attached to the first screw body 17 and with the other end thereof attached to the first area 13 of the patient's teeth in any typical manner now apparent to those skilled in the art.

The appliance 11 includes a second screw body 31 having an internally threaded bore 33. The second screw body 31 may consist of a rigid metal body having a smooth surface and rounded corners, etc., as will now be apparent to those skilled in the art. The threaded bore 33 is preferably located through the longitudinal center of the screw body 31. The screw body 31 preferably has a first unthreaded bore 35 extending therethrough parallel to and on one side of the threaded bore 33 and a second unthreaded bore 37 extending therethrough parallel to and on the other side of the threaded bore 33 as clearly shown in FIG. 3.

The appliance 11 includes a second retention means 39 attached to the second screw body 31 for securing or attaching the second screw body 31 relative to the second area 15 of the patient's teeth. The second retention means 39 may consist of a first arm member 41 and a second arm member 43 attached at one end to the second screw body 31 and attachable at the other end to the second area 15 of the patient's teeth. More specifically, each arm member 41, re may consist of a substantially rigid but bendable metal rod or the like with one end thereof soldered or otherwise fixedly attached to the second screw body 31 and with the other end thereof attached to the second area 15 of the patient's teeth in any typical manner now apparent to those skilled in the art.

The appliance 11 includes a screw spindle 45 having an externally threaded first end 47 for being screwed into the internally threaded bore 19 of the first screw body 17 and having an externally second end 49 for being screwed into the internally threaded bore 33 of the second screw body 31. The appliance 11 is designed so that rotation of the screw spindle 45 will cause the first and second screw bodies 17, 31 to move relative to one another. More specifically, the threaded bores 19, 33 preferably have oppositely-handed threads as do the first and second ends 47, 49 so that first and second ends 47, 49 are counter-rotating as will now be apparent to those skilled in the art. The screw spindle 45 preferably has a midportion 51 between the first and second ends 47, 49 adapted to aid in the manual rotation of the screw spindle 45. More specifically, the midportion 51 may have one or more transverse apertures 53 therethrough for receiving the end of a elongated rod-like tool 55 (see FIG. 2) to allow manual rotation of the screw spindle 45 as will now be apparent to those skilled in the art. The screw spindle 45 may be machined out of metal, etc., as will now be apparent to those skilled in the art. Each screw body 17, 31 may have a notch portion 56 therein for accommodating a portion of the midportion 51 of the screw spindle 45 when the appliance 11 is in a closed position as shown in FIG. 1.

The appliance 11 includes fill means 57 coating the externally threaded first and second ends 47, 49 of the screw spindle 45 for preventing the externally threaded first and second ends 47, 49 of the screw spindle 45 from inadvertently rotating within the internally threaded bores 19, 33 of the screw bodies 17, 31. The fill means 57 may include a synthetic resin polymer coating on the externally threaded first and second ends 47, 49 of the screw spindle 45. More specifically, the fill 57 may include a fluorocarbon resin coating on the externally threaded first and second ends 47, 49 of the screw spindle 45. Preferably, the fill means 57 includes a Teflon coating on the externally threaded first and second ends 47, 49 of the screw spindle 45.

Figure 2:
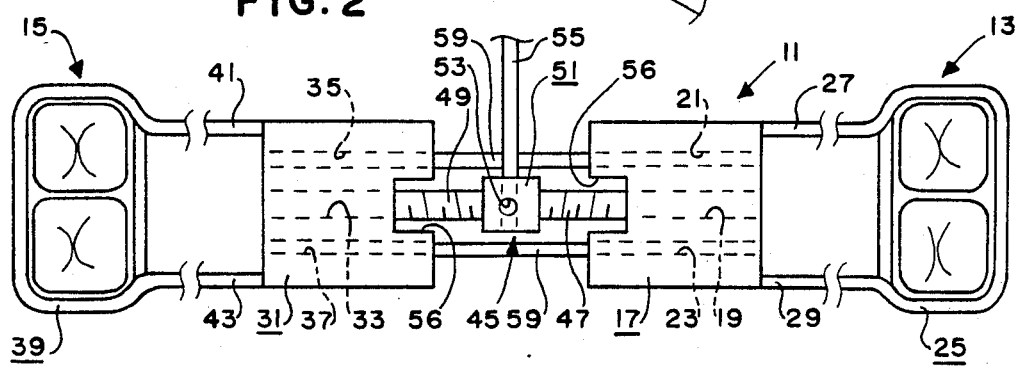
FIG. 2 is a somewhat diagrammatic plan view thereof within a patient's mouth.
Figure 3:
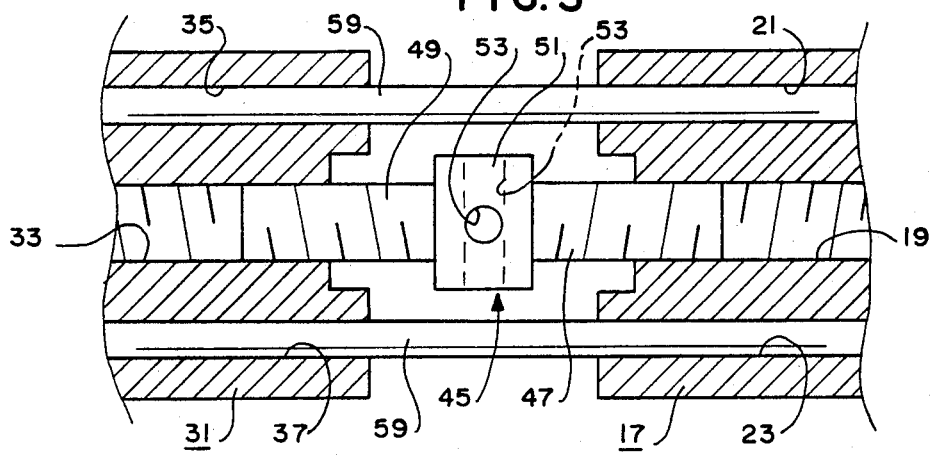
FIG. 3 is an enlarged sectional view of a portion thereof.
Figure 4:
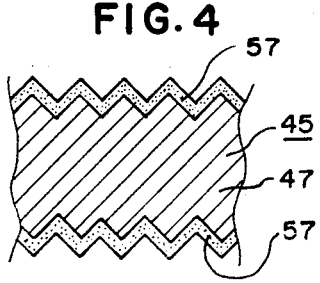
FIG. 4 is an enlarged sectional view of a portion thereof.
Figure 5:
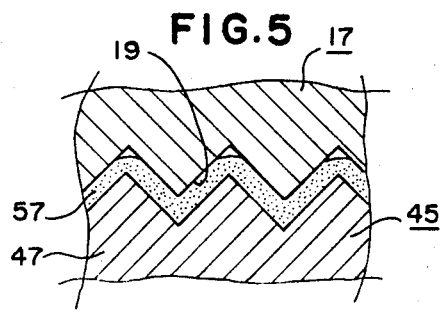
FIG. 5 is an enlarged sectional view of a portion thereof.

The appliance 11 preferably includes a pair of guide pin members or stabilizer rods 59 extending between the first and second screw bodies 17, 31 and slidably positioned in at least one of the respective bores 21, 23, 35, 37 as clearly shown in FIGS. 2 and 3 for helping maintain alignment between the screw bodies 17, 31 in a manner as will now be apparent to those skilled in the art.

The basic construction of the appliance 11 may be identical to other prior art fixed-type orthodontic expansion screw appliances with the exception of the fill means 57. Thus, for example, the screw bodies 17, 31, retention means 25, 29, screw spindle 45 and stabilizer rods 49 may be machined or otherwise formed out of metal. The fill means 57 may be applied to the first and second ends 47, 49 of the screw spindle 45 in any manner now apparent to those skilled in the art such as, for example, by dipping. High-temperature soldering is then used in fabricating the appliance 11 (e.g., securing the retention means 25, 39 to the screw bodies 17, 31, etc.), thus eliminating the use of any plastic in the appliance 11.

Although the present invention has been described and illustrated with respect to a preferred embodiment, it is not to be so limited since modifications and changes can be made therein which are within the full intended scope of the invention.

I claim:

1. An orthodontic expansion screw appliance for being secured to first and second areas of a patient's teeth; said appliance comprising:
   (a) a first screw body having an internally threaded bore;
   (b) first retention means attached to said first screw body for securing said first screw body relative to the first area of the patient's teeth;
   (c) a second screw body having an internally threaded bore;
   (d) second retention means attached to said second screw body for securing said second screw body relative to the second are of the patient's teeth;
   (e) a screw spindle having an externally threaded first end for being screwed into said internally threaded bore of said first screw body and having an externally threaded second end for being screwed into said internally threaded bore of said second screw body: rotation of said screw spindle causing said first and second screw bodies to move relative to one another; and
   (f) fill means coating said externally threaded first and second ends of said screw spindle for preventing said externally threaded first and second ends of said screw spindle from inadvertently rotating within said internally threaded bores of screw bodies.

2. The appliance of claim 1 in which said fill means includes a fluorocarbon resin coating on said externally threaded first and second ends of said screw spindle.

3. The appliance of claim 1 in which said fill means includes a synthetic resin polymer coating on said externally threaded first and second ends of said screw spindle.

4. The appliance of claim 1 in which said fill means includes a fluorocarbon resin coating on said externally threaded first and second ends of said screw spindle.

5. An orthodontic expansion screw appliance for being secured to first and second areas of a patient's teeth; said appliance comprising:
   (a) a first screw body having an internally threaded bore;
   (b) first retention means attached to said first screw body for attaching said first screw body relative to the first area of the patient's teeth;
   (c) a second screw body having an internally threaded bore;
   (d) second retention means attached to said second screw body for attaching said second screw body relative to the second area of the patient's teeth;
   (e) a screw spindle having an externally threaded first end for being screwed into said internally threaded bore of said first screw body and having an externally threaded second end for being screwed into said internally threaded bore of said second screw body; rotation of said screw spindle causing said first and second screw bodies to move relative to one another;
   (f) a first guide pin member extending between said screw bodies;
   (g) a second guide pin member extending between said screw bodies; and
   (h) a fluorocarbon resin coating on said externally threaded first and second ends of said screw spindle for preventing said externally threaded first and second ends of said screw spindle from inadvertently rotating within said internally threaded bores of said screw bodies.

6. An improved orthodontic expansion screw appliance for being secured to first and second areas of a patient's teeth; said appliance including a first screw body having an internally threaded bore; first retention means attached to said first screw body for attaching said first screw body relative to the first area of the patient's teeth; a second screw body having an internally threaded bore; second retention means attached to said second screw body for attaching said second screw body relative to the second area of the patient's teeth; and a screw spindle having an externally threaded first end for being screwed into said internally threaded bore of said first screw body and having an externally threaded second end for being screwed into said internally threaded bore of said second screw body; rotation of said screw spindle causing said first and second screw bodies to move relative to one another; wherein the improvement comprises fill means coating said externally threaded first and second ends of said screw spindle for preventing said externally threaded first and second ends of said screw spindle from inadvertently rotating within said internally threaded bores of said screw bodies.

* * * * *